United States Patent [19]

Giaever

[11] 3,979,184

[45] Sept. 7, 1976

[54] DIAGNOSTIC DEVICE FOR VISUALLY DETECTING PRESENCE OF BIOLOGICAL PARTICLES

[75] Inventor: Ivar Giaever, Schenectady, N.Y.

[73] Assignee: General Electric Company, Schenectady, N.Y.

[22] Filed: May 27, 1975

[21] Appl. No.: 580,603

[52] U.S. Cl. .......................... 23/253 TP; 23/230 B; 128/2 R; 204/192; 424/12; 427/250; 428/336; 428/434; 428/469; 428/474

[51] Int. Cl.$^2$ .......................................... G01N 33/16

[58] Field of Search ........ 23/230 B, 253 R, 253 TP, 23/259; 424/12; 204/192

[56] References Cited

UNITED STATES PATENTS

| | | | |
|---|---|---|---|
| 3,271,179 | 9/1966 | Smith, Jr. | 204/192 X |
| 3,530,055 | 9/1970 | Maissel | 204/192 |
| 3,691,045 | 9/1972 | Lieberman | 204/192 |
| 3,853,467 | 12/1974 | Giaever | 23/253 R X |

OTHER PUBLICATIONS

M. Francon, "Modern Applications of Physical Optics," pp. 19–21, Interscience, New York, 1963.

*Primary Examiner*—Morris O. Wolk
*Assistant Examiner*—Sidney Marantz
*Attorney, Agent, or Firm*—Leo I. MaLossi; Joseph T. Cohen; Jerome C. Squillaro

[57] ABSTRACT

Devices for the detection of biological particles, particularly proteins. Such devices comprise a non-transparent surface of metal (solid metal or a non-transparent coating of metal on some different substrate) covered with a thin transparent first layer of dielectric material, which in turn has a transparent second layer of metal adhered over the outer surface thereof, the transparent layer preferably being in the form of metal globules or metal islets. The detection device as provided to the user will usually have a monomolecular layer of biological particles applied over at least a portion of the transparent layer of metal. Interference of light is obtained useful in distinguishing between monomolecular layers and multi-molecular layers with the unaided eye, when the non-transparent surface metal reflects light relatively poorly and is at least approximately matched to the light reflecting ability of the dielectric material forming the transparent layer thereover.

15 Claims, 1 Drawing Figure

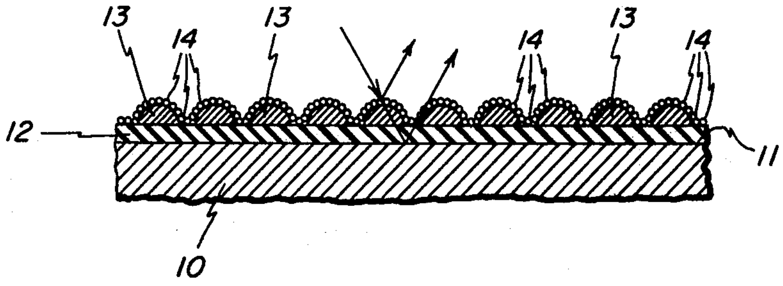
13
14
13
14
13
14
12
11
10

DIAGNOSTIC DEVICE FOR VISUALLY DETECTING PRESENCE OF BIOLOGICAL PARTICLES

BACKGROUND OF THE INVENTION

This invention relates to the detection of biological particles by the utilization of the phenomenon by which such biological particles interact specifically either immunologically or non-immunologically.

Constructions of diagnostic devices for use in the immunological detection of proteins are disclosed in the related copending U.S. Applications of Giaever, Ser. No. 384,113, filed July 30, 1973 (now abandoned) and Ser. No. 445,204, (now U.S. Pat. No. 3,926,564) filed Feb. 25, 1974. In both of these constructions the outer surface consists of a layer of preselected proteins specifically interactive with the protein of interest. In Ser. No. 384,113, the substrate surface to which the preselected protein layer is applied is preferably metallic. In Ser. No. 445,204 the substrate surface to which the preselected protein layer is applied is made up predominately of metallic oxide, which metallic oxide may contain minute matallic particles. The aforementioned copending applications are assigned to the assignee of this invention and are incorporated herein by reference.

The preselected protein layer absorbs on to the surface of the substrate in a monomolecular layer. When a suspected solution is to be tested for the presence or absence of the protein of interest, the monomolecular protein layer is placed in contact with the solution for a sufficiently long period of time to permit the specific reaction to occur if the protein of interest is present. Wherever the specific reaction occurs, the resulting complex between the initial protein layer and the protein of interest results in a bimolecular protein layer. No protein other than the protein of interest will adhere to the initial protein layer. Detection of the presence of a bimolecular layer as contrasted to a monomolecular layer follows.

Those publications related to the present invention primarily as background are "Optical Measurement of the Thickness of a Film Adsorbed from a Solution" by Irving Langmuir et al. [Journal of the American Chemical Society, Vol. 59 (July–Dec. 1937) page 1406]; "Immunological Reactions Carried Out At a Liquid-Solid Interface" by A. Rothen et al. [Helvetica Chimica Acta - Vol. 54, Fasc 4 (1971)-Nr. 123, pages 1208–1217]; "Blood Coagulation Studies With the Recording Ellipsometer" by L. Vroman [National Bureau of Standards Miscellaneous Publication 256, September 1964]; "Immunological Reactions Between Films of Antigen and Antibody Molecules" by A. Rothen [Journal of Biological Chemistry, Vol. 168, pages 75–97 (April, May 1947)]; "Findings With the Recording Ellipsometer Suggesting Rapid Exchange of Specific Plasma Proteins at Liquid/Solid Interfaces" by L. Vroman et al. [Surface Science 16 (1969), pages 438–446]; "Immunologic and Enzymatic Reactions Carried Out at a Solid-Liquid Interface" by Alexandre Rothen [Physiological Chemistry and Physics, 5, (1973) pages 243–258]; "Interactions Among Human Blood Proteins at Interfaces" by Leo Vroman et al. [Federation Proceedings, Vol. 30, No. 5 (Sept.–Oct. 1971) pages 1494–1502]; "The Antibody-Antigen Reaction: A Visual Observation" by Ivar Giaever [The Journal of Immunology, Vol. 110, No. 4 (May 1973)

pages 1424–1426]; "Effects of Hydrophobic Surfaces Upon Blood Coagulation" by L. Vroman [Thromb. Diath, Haemorrhag., Vol. 10, pages 455–493 (1964)] and "Three Simple Ways to Detect Antibody-Antigen Complex on Flat Surfaces" by A. L. Adams et al. [Journal of Immunological Methods 3 (1973) pages 227–232].

The term "biological particle" is intended to encompass smaller proteins (e.g. plasma proteins, antigens, antibodies, lactins) and bodies of proteinaceous material (e.g. viruses, bacteria, cells) capable of stimulating antibody production, when injected into an animal, and/or having the property of interacting specifically either immunologically or non-immunologically.

DESCRIPTION OF THE INVENTION

Diagnostic devices according to this invention comprise a non-transparent metal surface (solid metal or a non-transparent coating of a metal on some different substrate) covered with a thin, transparent layer of dielectric material, which in turn has a transparent second layer of metal, preferably in the form of metal globules or islets, adhered over the outer surface thereof. The detection device as normally provided to the user will have a monomolecular layer of biological particles applied over the surface of the second layer. Interference of light is obtained that may be used to distinguish with the unaided eye between a monomolecular layer and multimolecular layers applied to the device in diagnostic use, when the non-transparent surface metal selected is one that reflects light relatively poorly and is at least approximately matched to the light reflecting ability of the dielectric material forming the transparent layer thereover.

BRIEF DESCRIPTION OF THE DRAWING

The subject matter of the instant invention for which protection is sought is presented as claims at the conclusion of the written description of the invention set forth herein. The description sets forth the manner and process of making and using the invention and the accompanying drawing forms part of the description schematically illustrating one embodiment. The view shown is an elevational cross-section taken through a portion of the substrate and the plurality of layers applied over a surface thereof to constitute a diagnostic device.

MANNER AND PROCESS OF MAKING AND USING THE INVENTION

Referring now to the drawing, substrate 10, which is either a solid metal sheet or a non-transparent coating of a metal adhered to a base of some different material, has bonded directly to surface 11 thereof a layer 12 of dielectric material. In the case in which the metal is applied to a different base, the base may be of glass, another metal, plastic, etc.

Adhered directly to the outer surface of transparent layer 12 is a second transparent layer of a second metal. Preferably, this layer of the second metal is in the form of globules 13 adhered to layer 12. The nature of this coating as a discontinuous layer on a microscopic scale is shown in the drawing. This layer of second metal may for some applications be in the form of a continuous transparent film. Next, a monomolecular layer of biological particles 14 is applied over all or a portion of the area of the second transparent layer of metal.

While metals characteristically reflect visible light well, the metal of surface 11 must be a comparatively poor reflector of light. Also, preferably this metal will be one, which anodizes readily or is readily oxidized. Examples of such metals are titanium, niobium, vanadium, bismuth, zirconium and tantalum. Metals such as aluminum and silver reflect light too well to be utilized as the non-transparent metal providing surface 11.

While it may be particularly convenient to provide dielectric layer 12 as an oxide of the non-transparent first metal, it is also contemplated that layer 12 may be a totally different material, e.g. a polymer or copolymer, adhered to the first metal. The application of polymer and copolymer coatings by photopolymerization to a variety of both metallic and non-metallic substrates are described in U.S. Pat. No. 3,522,076 — Wright and U.S. Pat. No. 3,635,750 — Wright. Both of these Wright patents are incorporated by reference.

Still other materials may be applied as dielectric layer 12 e.g. a dielectric layer can be applied by evaporation of magnesium fluoride.

If the first metal is applied as a layer over a different substrate e.g. a layer of titanium on a plastic substrate, such as polystyrene, the metal layer should be sufficiently thick so that the layer is not transparent to visible light and yet not so thick that there is any danger of it not remaining firmly adhered to the substrate during commonly encountered changes in temperature. A suitable thickness of titanium metal in such a construction has been found to about 2000 (angstroms (A).

In a construction in which the transparent second layer (metal) is deposited on dielectric layer 12 in the form of globules, the relationship between dielectric layer thickness and metal globule diameter should bear a relationship to each other. Thus, the dielectric layer 12 should range in thickness from about 5 A to about 500 A. The diameter of metal globules relates thereto by ranging from about 5000 A (coupled with the minimum thickness dielectric layer) to about 200 A (coupled with the maximum dielectric layer thickness). In a system in which the first metal is titanium, the dielectric layer is titanium oxide and the second metal layer is of indium deposited as globules or islets, the preferred combination is a titanium oxide layer thickness of about 200 A and an average diameter of about 1000 A for the indium globules.

The non-transparent first metal need not be a single metal, particularly in the construction in which a metal layer is deposited over the surface of a different base or substrate. Thus, it has been found particularly advantageous to co-deposit titanium and bismuth, this combination being easier to anodize than titanium alone. In an exemplary construction a microscope slide was provided with a first metal layer as a mixed deposition by the co-evaporation of titanium and bismuth. After deposition, the coated slide was anodized in a 0.05N solution of sodium hydroxide at 8 volts. This anodized surface was then covered with very small indium particles in the 500 A diameter range. In a variation that was found to give excellent readout characteristics, a glass slide base was first roughened slightly by sandblasting before the application of the first metal layer thereto.

The preferred metals for the metallic second layer are those which do not wet the surface of the preceding dielectric layer and have high mobility on this surface. These material characteristics promote deposition in the form of globules. Deposition is normally accomplished by evaporation of the metal in a vacuum. Examples of suitable metals for the metallic second layer are indium, gold, silver, tin and lead. It is to be noted in connection with this invention that both tin (second metal layer) and bismuth (first metal layer) are not stable as pure materials in salt solutions for long periods of time. There are, however, many applications for these diagnostic devices in which such exposure is not required.

The combination as described herein of the first metal surface, the dielectric layer and the second layer of metal produces very good interference colors from visible light incident thereon. No explanation for this is yet available due to the complexity of the physics involved. To a first approximation it can be considered that the dielectric layer in combination with the second layer of metal acts as a dielectric layer with a high index of refraction. Thin layers of protein adsorbed to the outer surface of such units change the interference colors and, therefore, become visible. The outer layer of metal must be transparent, preferably passing from about 60 to about 70% of the light incident thereon. Having the second metal surface be non-continuous is the preferred construction. For best results the reflection from the metal globules should match the reflection from the underlying (first metal) reflecting surface, i.e., for strong interference colors the same amount of light should be reflected from the globules as is reflected from surface 11.

Diagnostic devices prepared according to this invention are particularly of value when employed according to the amplification techniques described in U.S. patent application Ser. No. 388,407 — Golibersuch (now U.S. Pat. No. 3,904,367) assigned to the assignee of the instant invention. The methods set forth therein for increasing the sensitivity of immunological film detection are incorporated by reference.

This amplification technique in which a plurality of specific immunological reactions are performed in sequence is particularly effective, when performed with the diagnostic devices of this invention. With the construction disclosed and claimed herein as a plurality of successive antigen-antibody films are built-up, contrast between multi-layer protein films and the monomolecular layer protein film initially applied increases at least through the fourth stage. The amplifying capabilities of the diagnostic device construction of this invention is shown is examples to follow. In both of the following examples the layered structure (before the application of the protein monomolecular layer) was as follows: a glass microscope slide was coated with about 2000 A of titanium; this film was anodized in 0.05N NaOH at 8 volts and then covered with vapor-deposited indium particles averaging about 400 A in diameter.

EXAMPLE 1

A monomolecular layer of carcino-embryonic antigen (Hoffmann-LaRoche, Inc.) was applied to a small part of the surface area of the layered structure to complete the diagnostic device. When the coating had been washed to remove excess carcino-embryonic antigen (CEA) and dried, the CEA was contacted with goat serum containing antibodies to CEA being incubated for 16 hours. Without washing the slide it was contacted with rabbit serum containing about 20 micrograms/ml of antibodies to the goat antibodies. After a period of contact of about 15 minutes, the slide without washing was contacted with goat serum having a concentration of 200 micrograms/ml of antibodies to the rabbit antibodies for about 15 minutes. The slide was then washed, dried and then examined. The presence of the multiple layers of protein that had builtup over the portion of the CEA layer, that had received the first exposure to goat serum (containing antibodies to CEA) was clearly visible to the unaided eye even when this goat serum was diluted 1:30,000,000. This represents a capability for detecting antibodies in a concentration of less than 0.1 nanogram/ml.

EXAMPLE 2

A monomolecular layer of bovine serum albumin (BSA) was applied over a small portion of the surface area of the layered structure, washed and dried. Next, the BSA was contacted over a portion thereof with rabbit anti-serum BSA (Miles Laboratory) and incubated for about 4 hours. Next, the BSA layer including the previously exposed portion was contacted with goat serum containing with a concentration of antibodies of about 20 micrograms/ml to the antibodies to be assayed. After 15 minutes the slide was exposed to rabbit serum containing a concentration of 200 micrograms/ml of antibodies to the goat antibodies. After a period of about 15 minutes, the slide was washed, dried and examined. The region in which the BSA was exposed during the antibody assay accumulated three more monomolecular layers over the area of initial exposure as the result of the sequence of exposures. The presence of the multiple layers was readily apparent to the unaided eye even when the initial rabbit anti-serum was diluted 1:2,000,000, the equivalent of having a concentration of antibody in the initial rabbit serum of 1 nanogram/ml.

The best mode contemplated employs a plastic substrate (e.g. polystyrene) having a non-transparent layer about 2000 A thick of titanium and bismuth co-deposited thereover. The dielectric layer is produced by anodizing the titanium/bismuth layer. Subsequently, indium is deposited thereover as globules about 500 A in diameter. Thereafter, a monomolecular layer of biological particles is applied over the indium particles.

What I claim as new and desire to secure by Letters Patent of the United States is:

1. A diagnostic device for detecting the presence or absence of select biological particles in a liquid sample consisting of:

a substrate member, at least one face of which is a non-transparent surface of metal, said metal surface being a comparatively poor reflector of light, a thin, transparent first layer of dielectric material adhered to said surface, a transparent second layer of metal adhered to the outer face of said first layer, a monomolecular layer of biological particles specific to the select biological particles overlying at least a portion of said second layer.

2. The diagnostic device of claim 1 wherein the substrate member comprises a metal coating on a non-metallic base.

3. The diagnostic device of claim 2 wherein the base is plastic.

4. The diagnostic device of claim 2 wherein the base is glass.

5. The diagnostic device of claim 1 wherein metal for the non-transparent surface is selected from the group consisting of titanium, niobium, vanadium, bismuth, zirconium, tantalum and mixtures thereof.

6. The diagnostic device of claim 5 wherein the non-transparent surface is titanium.

7. The diagnostic device of claim 5 wherein the non-transparent surface is titanium and bismuth.

8. The diagnostic device of claim 1 wherein the light reflecting ability of the non-transparent surface metal is approximately matched to the light reflecting ability of the dielectric material.

9. The diagnostic device of claim 1 wherein the dielectric material is metal oxide wherein the metal portion is derived from the non-transparent surface.

10. The diagnostic device of claim 1 wherein the dielectric material is a polymer polymerized in situ.

11. The diagnostic device of claim 1 wherein the transparent second layer is non-continuous and in the form of globules.

12. The diagnostic device of claim 11 wherein the transparent second layer is indium.

13. The diagnostic device of claim 11 wherein the dielectric layer is about 200 Angstroms thick and the globules of the transparent layer are about 1000 Angstroms in diameter.

14. The diagnostic device of claim 11 wherein the transparent second layer transmits about 60% to about 70% of the light incident thereon.

15. The diagnostic device of claim 1 wherein the transparent second layer is continuous.

* * * * *